(12) United States Patent
Bjorkman et al.

(10) Patent No.: US 8,859,726 B2
(45) Date of Patent: Oct. 14, 2014

(54) AFFINITY CHROMATOGRAPHY MATRIX

(75) Inventors: Tomas Bjorkman, Uppsala (SE); Gustav Rodrigo, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 0 days.

(21) Appl. No.: 13/990,135

(22) PCT Filed: Nov. 28, 2011

(86) PCT No.: PCT/SE2011/051432
§ 371 (c)(1),
(2), (4) Date: May 29, 2013

(87) PCT Pub. No.: WO2012/074463
PCT Pub. Date: Jun. 7, 2012

(65) Prior Publication Data
US 2013/0245224 A1 Sep. 19, 2013

Related U.S. Application Data

(60) Provisional application No. 61/417,494, filed on Nov. 29, 2010.

(51) Int. Cl.
*C07K 1/22* (2006.01)
*C07K 1/16* (2006.01)
*C07K 16/00* (2006.01)
*B01D 15/38* (2006.01)
*B01J 20/32* (2006.01)
*C07K 16/06* (2006.01)
*B01J 20/286* (2006.01)

(52) U.S. Cl.
CPC .............. *C07K 1/22* (2013.01); *B01D 15/3809* (2013.01); *B01J 20/3274* (2013.01); *C07K 16/065* (2013.01); *B01J 20/3208* (2013.01); *B01J 20/286* (2013.01); *B01J 20/3242* (2013.01)
USPC ........ 530/324; 530/387.1; 530/350; 502/400; 502/403

(58) Field of Classification Search
CPC .............. B01J 20/3274; B01J 20/3268; B01J 20/3242; B01D 15/265; B01D 15/08; B01D 15/00; C07K 1/22; C07K 1/16; C07K 1/14; C07K 16/065; C07K 16/00
See application file for complete search history.

(56) References Cited

U.S. PATENT DOCUMENTS

| 5,362,859 A | 11/1994 | Zale |
| 2006/0194950 A1* | 8/2006 | Hober et al. .................. 530/350 |
| 2006/0194955 A1 | 8/2006 | Hober et al. |

FOREIGN PATENT DOCUMENTS

| WO | WO 2008/039141 | 4/2008 |
| WO | WO 2010/080065 | 7/2010 |

OTHER PUBLICATIONS

Ghose, S., et al., Biotechnology Engineering, 2006, vol. 96, pp. 768-779.

* cited by examiner

*Primary Examiner* — Karlheinz R Skowronek
*Assistant Examiner* — Catherine Mader

(57) ABSTRACT

The present invention relates to a method of separating one or more immunoglobulin containing proteins from a liquid. The method includes first contacting the liquid with a separation matrix comprising ligands immobilised to a support; allowing the immunoglobulin containing proteins to adsorb to the matrix by interaction with the ligands; followed by an optional step of washing the adsorbed immunoglobulin containing proteins; and recovering said immunoglobulin containing proteins by contacting the matrix with an eluent which releases the proteins. The method improves upon previous separation methods in that each of the ligands comprises one or more of a protein A domain (E, D, A, B, C), or protein Z, or a functional variant thereof, with at least one of the monomers having a substitution of the C-terminal most proline residue after the third alpha-helix.

13 Claims, 4 Drawing Sheets

```
         10         20         30         40         50
         |          |          |          |          |
VDAKFDKEQQ NAFYEILHLP NLNEEQRNGF IQSLKDDPSQ SANLLAEAKK LNDAQAPK
<Helix 1 >            <  Helix 2  >        <  Helix 3  >
```

Figure 1

IgG heavy chains

IgG heavy chains

Protein A (five domains, EDABC)

```
                                                            (N-terminus)
          QQNAFYQVLNMPNLNADQRNGFIQSLKDDPSQSANVLGEAQKLNDSQAPK  (E) SEQ ID No: 4
ADAQQNNFNKDQQSAFYEILNMPNLNEAQRNGFIQSLKDDPSQSTNVLGEAKKLNESQAPK  (D) SEQ ID No: 5
ADNNFNKEQQNAFYEILNMPNLNEEQRNGFIQSLKDDPSQSANLLSEAKKLNESQAPK    (A) SEQ ID No: 6
ADNKFNKEQQNAFYEILHLPNLNEEQRNGFIQSLKDDPSQSANLLAEAKKLNDAQAPK    (B) SEQ ID No: 7
ADNKFNKEQQNAFYEILHLPNLTEEQRNGFIQSLKDDPSVSKEILAEAKKLNDAQAPK    (C) SEQ ID No: 8
                                                            (C-terminus)
```

Figure 2d

AFFINITY CHROMATOGRAPHY MATRIX

CROSS- REFERENCE TO RELATED APPLICATIONS

This application is a filing under 35 U.S.C. 371 of international application number PCT/SE2011/051432, filed Nov. 28, 2011, published on Jun. 7, 2012 as WO 2012/074463, which claims priority to U.S. provisional patent application number 61/417,494 filed Nov. 29, 2010.

FIELD OF THE INVENTION

The present invention relates to the field of affinity chromatography, and more specifically to separation matrix containing ligand containing one or more of a protein A domain (E, D, A, B, C), or protein Z, with an amino acid substitution for the C-terminal most proline residue in at least one of the monomers. The invention also relates to methods for the separation of proteins of interest with aforementioned matrix, with the advantage of increased capacity.

BACKGROUND OF THE INVENTION

Immunoglobulins represent the most prevalent biopharmaceutical products in either manufacture or development worldwide. The high commercial demand for and hence value of this particular therapeutic market has lead to the emphasis being placed on pharmaceutical companies to maximise the productivity of their respective mAb manufacturing processes whilst controlling the associated costs.

Affinity chromatography is used in most cases, as one of the key steps in the purification of these immunoglobulin molecules, such as monoclonal or polyclonal antibodies. A particularly interesting class of affinity reagents is proteins capable of specific binding to invariable parts of an immunoglobulin molecule, such interaction being independent on the antigen-binding specificity of the antibody. Such reagents can be widely used for affinity chromatography recovery of immunoglobulins from different samples such as but not limited to serum or plasma preparations or cell culture derived feed stocks. An example of such a protein is staphylococcal protein A, containing domains capable of binding to the Fc and Fab portions of IgG immunoglobulins from different species.

Staphylococcal protein A (SpA) based reagents have due to their high affinity and selectivity found a widespread use in the field of biotechnology, e.g. in affinity chromatography for capture and purification of antibodies as well as for detection. At present, SpA-based affinity medium probably is the most widely used affinity medium for isolation of monoclonal antibodies and their fragments from different samples including industrial feed stocks from cell cultures. Accordingly, various matrices comprising protein A-ligands are commercially available, for example, in the form of native protein A (e.g. Protein A SEPHAROSE™, GE Healthcare, Uppsala, Sweden) and also comprised of recombinant protein A (e.g. rProtein A SEPHAROSE™, GE Healthcare). More specifically, the genetic manipulation performed in the commercial recombinant protein A product is aimed at facilitating the attachment thereof to a support.

These applications, like other affinity chromatography applications, require comprehensive attention to definite removal of contaminants. Such contaminants can for example be non-eluted molecules adsorbed to the stationary phase or matrix in a chromatographic procedure, such as non-desired biomolecules or microorganisms, including for example proteins, carbohydrates, lipids, bacteria and viruses. The removal of such contaminants from the matrix is usually performed after a first elution of the desired product in order to regenerate the matrix before subsequent use. Such removal usually involves a procedure known as cleaning-in-place (CIP), wherein agents capable of eluting contaminants from the stationary phase are used. One such class of agents often used is alkaline solutions that are passed over said stationary phase. At present the most extensively used cleaning and sanitising agent is NaOH, and the concentration thereof can range from 0.1 up to e.g. 1 M, depending on the degree and nature of contamination. This strategy is associated with exposing the matrix for pH-values above 13. For many affinity chromatography matrices containing proteinaceous affinity ligands such alkaline environment is a very harsh condition and consequently results in decreased capacities owing to instability of the ligand to the high pH involved.

An extensive research has therefore been focussed on the development of engineered protein ligands that exhibit an improved capacity to withstand alkaline pH-values. For example, Gülich et al. (Susanne Gülich, Martin Linhult, Per-Åke Nygren, Mathias Uhlén, Sophia Hober, Journal of Biotechnology 80 (2000), 169-178) suggested protein engineering to improve the stability properties of a Streptococcal albumin-binding domain (ABD) in alkaline environments. Gülich et al. created a mutant of ABD, wherein all the four aspargine residues have been replaced by leucine (one residue), asparte (two residues) and lysine (one residue). Further, Gülich et al. report that their mutant exhibits a target protein binding behaviour similar to that of the native protein, and that affinity columns containing the engineered ligand show higher binding capacities after repeated exposure to alkaline conditions than columns prepared using the parental non-engineered ligand. Thus, it is concluded therein that all four asparagine residues can be replaced without any significant effect on structure and function.

Recent work shows that changes can also be made to protein A (SpA) to effect similar properties. US patent application publication US 2005/0143566 discloses that when at least one asparagine residue is mutated to an amino acid other than glutamine or aspartic acid, the mutation confers an increased chemical stability at pH-values of up to about 13-14 compared to the parental SpA, such as the B-domain of SpA, or Protein Z, a synthetic construct derived from the B-domain of SpA (U.S. Pat. No. 5,143,844). The authors show that when these mutated proteins are used as affinity ligands, the separation media as expected can better withstand cleaning procedures using alkaline agents. US 2006/0194955 shows that the mutated ligands can better withstand proteases thus reducing ligand leakage in the separation process. Another publication, US 2006/0194950 shows that the alkali stable SpA domains can be further modified such that the ligands lacks affinity for Fab but retains Fc affinity, for example by a G29A mutation.

Historically the native protein A containing 5 IgG binding domains was used for production of all protein A affinity media. Using recomenband technology a number of protein A construct have been produced all containing 4 or 5 IgG binding domains. A recent study showed that dimeric ligands have a similar, or increased binding capacity compared to tetrameric ligands (WO 2010/080065).

There is still a need in this field to obtain a separation matrix containing protein ligands having an increased binding capacity.

SUMMARY OF THE INVENTION

One object of the present invention is to provide protein ligands capable of binding immunoglobulins, such as IgG, IgA and/or IgM, preferably via their Fc-fragments. These ligands carry a substitution of the C-terminal most proline residue, in at least one of the monomeric domains of protein A (E, D, A, C, C) or protein Z, after the third alpha-helix, thus have a higher binding capacity, as compared to ligands without the substitution. Preferably, the ligands are multimeric, i.e., containing more than one monomeric domains selected from protein A (E, D, A, C, C) and protein Z.

Another object of the invention is to provide an affinity separation matrix, which comprises the ligands capable of binding immunoglobulins, such as IgG, IgA and/or IgM, preferably via their Fc-fragments, as described above.

A further object of the invention is to provide a method for separating one or more immunoglobulin containing proteins, using the current affinity matrix. By using affinity ligands with the substitution, the method unexpectedly achieves increased binding capacity for the target molecules.

Thus the invention provides a method for either producing a purified product, such as a pure immunoglobulin fraction or alternatively a liquid from which the immunoglobulin has been removed, or to detect the presence of immunoglobulin in a sample. The ligands according to the invention exhibit an increased capacity, which renders the ligands attractive candidates for cost-effective large-scale operation.

One or more of the above-defined objects can be achieved as described in the appended claims.

BRIEF DESCRIPTION OF THE DRAWINGS

FIG. 1 shows the amino acid sequence of protein Z, with the proline at position 57 shown in bold (SEQ ID NO: 2).

FIG. 2d shows an alignment of the amino acid sequences from each of the five domains of protein A.

DETAILED DESCRIPTION OF THE INVENTION

Definitions

Figure 2A:
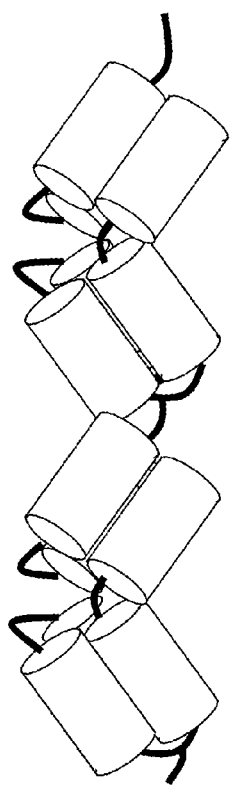
FIG. 2a shows a hypothetical tetrameric ligand structure, each monomer is a domain from protein A (E, D, A, B, C) or protein Z, which due to the presence of the C-terminal most proline in each monomer, contains a 60° bend between each domain.

The term "protein" is used herein to describe proteins as well as fragments thereof. Thus, any chain of amino acids that exhibits a three dimensional structure is included in the term "protein", and protein fragments are accordingly embraced.

The term "functional variant" of a protein means herein a variant protein, wherein the function, in relation to the invention defined as affinity and stability, are essentially retained. Thus, one or more amino acids those are not relevant for said function may have been exchanged.

The term "parental molecule" is used herein for the corresponding protein in the form before a mutation according to the invention has been introduced.

The term "structural stability" refers to the integrity of three-dimensional form of a molecule, while "chemical stability" refers to the ability to withstand chemical degradation.

The term "Fc fragment-binding" protein means that the protein is capable of binding to the Fc fragment of an immunoglobulin. However, it is not excluded that an Fc fragment-binding protein also can bind other regions, such as Fab regions of immunoglobulins.

In the present specification, if not referred to by their full names, amino acids are denoted with the conventional one-letter symbols.

Mutations are defined herein by the number of the position exchanged, preceded by the wild type or non-mutated amino acid and followed by the mutated amino acid. Thus, for example, the mutation of an asparagine in position 23 to a threonine is denoted N23T.

The present invention in one aspect relates to a method of separating one or more immunoglobulin containing proteins from a liquid, which method comprises (a) contacting the liquid with a separation matrix comprising ligands immobilised to a support; (b) allowing the immunoglobulin containing proteins to adsorb to the matrix by interaction with the ligands; (c) an optional step of washing the adsorbed immunoglobulin containing proteins; and (d) recovering the immunoglobulin containing proteins by contacting the matrix with an eluent which releases the proteins. The method provides increased binding capacity of the ligands to the immunoglobulin molecules by using a ligand, each of which comprises one or more domains (i.e., monomers) of staphylococcal Protein A (SpA) (E, D, A, B, C) or protein Z or a functional variant thereof, wherein the C-terminal most proline in at least one of the one or more domains have been substituted with any other amino acid.

The immunoglobulin-binding protein (i.e., ligand) can be any protein with a native immunoglobulin-binding capability, such as Staphylococcal protein A (SpA) or Streptococcal protein G (SpG), or recombinant proteins containing IgG-binding domains of these proteins. For a review of other such proteins, see e.g. Kronvall, G., Jonsson, K. Receptins: a novel term for an expanding spectrum of natural and engineered microbial proteins with binding properties for mammalian proteins, *J. Mol. Recognit.* 1999 January-February; 12(1):38-44. The ligands can comprise one of more of the E, D, A, B and C domains of SpA. More preferably the ligands comprise domain B of protein A or the engineered protein Z.

Every protein Z or protein A domain contains a proline close to the C-terminal (P57) (see e.g., FIG. 1, FIG. 2d, and SEQ ID NO. 1-8). Prolines are known to give turns in proteins due to their structure, i.e. the side-chain is linked to the alpha nitrogen. This link restricts to bonding angles of phi=~60°, thus giving a turn in the protein. A classical example is seen in the hinge of IgG, where prolines are found. Thus, when proline is present at the C-terminal, every domain of protein A or protein Z ends with a 60° angle in the bond, giving a turn between domains (FIG. 2a-2c)). The C-terminal most proline is neither involved in Fc-binding (Graille et al, PNAS 2000, 97 (10): 5399-5404; Deisenhofer, Biochemistry 1981, 20 (9): 2361-2370) nor part of an alpha helix (impossible for a proline).

Figure 2B:
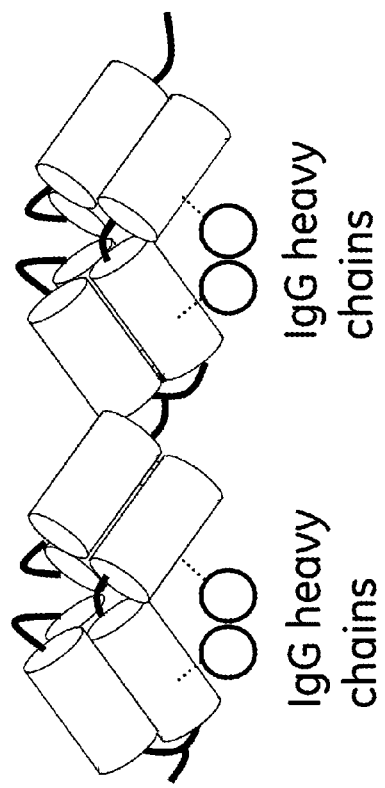
FIG. 2b shows hypothetical binding between the ligands and IgG where a single IgG binds to two monomeric domains (both Fc-chains represented by a circle, each binds to one monomeric domain).
Figure 2C:
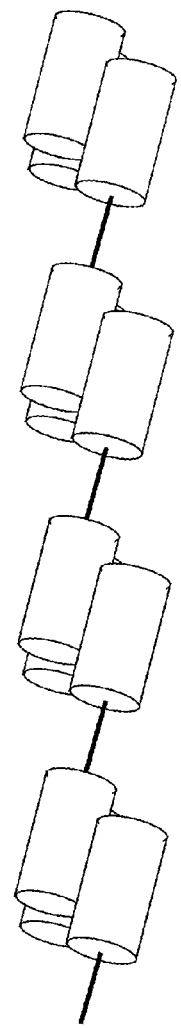
FIG. 2c shows a hypothetical, more linear and flexible multimeric ligand structure among the monomer domains due to the substitution of the C-terminal most proline in each domain with another amino acid residue.

Thus the protein A/protein Z ligand's poor usage of the monomeric domains (one out of two are used at total overloading) could be due to the structural limitation caused by the presence of the C-terminal proline in each domain, i.e., steric hindrance. There is a possibility that two domains in a ligand bind one IgG molecule, therefore blocking IgG access to every other domain (FIG. 2b). Such binding could also imply a stronger binding of IgG to the ligand. Certain embodiments of the invention substitute the C-terminal most proline (P57 of SEQ ID NO: 1 or 2) in each domain to achieve a higher usage of each domain, and thus an increased capacity of the ligand, possibly due to a more linear and/or flexible multimeric ligand structure among the monomeric domains (FIG. 2c).

As shown in FIG. 2d, the sequences among the five domains of Protein A are highly related. There are no deletions or insertion, and many of the substitutions are conservative changes with minimal potential change to the structure or function of the protein. For example, there are only four changes between the B domain and the C domain, over the entire 58 amino acid polypeptide. Thus, the C-terminal proline in each of these domains have a similar structural/functional contribution to protein A or ligand containing the domain. Similarly, changes of the proline cause a similar effect to the structure/function of the ligand containing such a change.

In certain embodiments, the proline is substituted with an amino acid that preferentially forms beta-sheets. Preferably, the proline is substituted for a bulky amino acid or amino acid giving "stiffness", e.g. Y, W, F, M, I, V, T. More preferably, the substitution is P57I.

In other embodiments, the proline is substituted with an amino acid that is prone to formation of alpha helices, e.g. E, A, L, H, M, Q, K.

In certain preferred embodiments, the parental molecule comprises the sequence defined by SEQ ID NO: 1-8, or any functional variance thereof.

In certain embodiments, the C-terminal most proline residue in at least one of the monomeric domains in a multimeric ligand is substituted. In other embodiments, the C-terminal most proline residue in all the monomeric domains in a multimeric ligand is substituted.

In one embodiment, the ligands are also rendered alkali-stable, such as by mutating at least one asparagine residue of at least one of the monomeric domains of the SpA domain B or protein Z to an amino acid other than glutamine. As discussed earlier, US patent application publication US 2005/0143566 discloses that when at least one asparagine residue is mutated to an amino acid other than glutamine or aspartic acid, the mutation confers the ligand an increased chemical stability at high pH (e.g., N23T). Further, affinity media including these ligands can better withstand cleaning procedures using alkaline agents. US 2006/0194955 shows that the mutated ligands can also better withstand proteases thus reducing ligand leakage in the separation process. The disclosures of these applications are hereby incorporated by reference in their entirety.

In another embodiment, the ligand(s) so prepared lack any substantial affinity for the Fab part of an antibody, while having affinity for the Fc part. Thus, in certain embodiments, at least one glycine of the ligands has been replaced by an alanine. US 2006/0194950 shows that the alkali stable domains can be further modified such that the ligands lacks affinity for Fab but retains Fc affinity, for example by a G29A mutation. The disclosure of the application is hereby incorporated by reference in its entirety. The numbering used herein of the amino acids is the conventionally used in this field, exemplified by the position on domain B of protein A, and the skilled person in this field can easily recognize the position to be mutated for each domain of E, D, A, B, C, or protein Z.

In an advantageous embodiment, the ligand is made of multimer copies of domain B, and the alkali-stability of domain B has been achieved by mutating at least one asparagine residue to an amino acid other than glutamine (e.g. N23T); and contains a mutation of the amino acid residue at position 29 of the alkali-stable domain B, such as a G29A mutation.

In another embodiment, the ligand is made of multimer copies of protein Z in which the alkali-stability has been achieved by mutating at least one asparagine residue to an amino acid other than glutamine. In an advantageous embodiment, the alkali-stability has been achieved by mutating at least the asparagine residue at position 23 to an amino acid other than glutamine.

As the skilled person in this field will easily understand, the substitution of P57, the mutations to provide alkaline-stability, and the G to A mutation may be carried out in any order of sequence using conventional molecular biology techniques. Further, the ligands can be expressed by a vector containing a nucleic acid sequence encoding the mutated protein ligands. Alternatively, they can also be made by protein synthesis techniques. Methods for synthesizing peptides and proteins of predetermined sequences are well known and commonly available in this field.

Thus, in the present invention, the term "alkali-stable domain B of Staphylococcal Protein A" means an alkali-stabilized protein based on Domain B of SpA, such as the mutant protein described in US patent application publications US 2005/0143566 and US 2006/0194950; as well as other alkali-stable proteins of other origin but having a functionally equivalent amino acid sequence.

As the skilled person will understand, the expressed protein should be purified to an appropriate extent before being immobilized to a support. Such purification methods are well known in the field, and the immobilization of protein-based ligands to supports is easily carried out using standard methods. Suitable methods and supports will be discussed below in more detail.

Accordingly, in one embodiment, a mutated protein according to the invention comprises at least about 75%, such as at least about 80% or preferably at least about 95%, of the sequence as defined in SEQ ID NOs: 1 or 2, with the proviso that the asparagine mutation is not in position 21.

In the present specification, SEQ ID NO: 1 defines the amino acid sequence of the B-domain of SpA:

Ala Asp Asn Lys Phe Asn Lys Glu Gln Gln Asn Ala

Phe Tyr Glu Ile Leu His Leu Pro Asn Leu Asn Glu

Glu Gln Arg Asn Gly Phe Ile Gln Ser Leu Lys Asp

Asp Pro Ser Gln Ser Ala Asn Leu Leu Ala Glu Ala

Lys Lys Leu Asn Asp Ala Gln Ala Pro Lys.

SEQ ID NO: 2 defines a protein known as protein Z:

Val Asp Asn Lys Phe Asn Lys Glu Gln Gln Asn Ala

Phe Tyr Glu Ile Leu His Leu Pro Asn Leu Asn Glu

Glu Gln Arg Asn Ala Phe Ile Gln Ser Leu Lys Asp

Asp Pro Ser Gln Ser Ala Asn Leu Leu Ala Glu Ala

Lys Lys Leu Asn Asp Ala Gln Ala Pro Lys.

Protein Z is a synthetic construct derived from the B-domain of SpA, wherein the glycine in position 29 has been exchanged for alanine, see e.g. Ståhl et al, 1999: Affinity fusions in biotechnology: focus on protein A and protein G, in The Encyclopedia of Bioprocess Technology: Fermentation, Biocatalysis and Bioseparation. M. C. Fleckinger and S. W. Drew, editors. John Wiley and Sons Inc., New York, 8-22.

In one embodiment, the above described mutant protein is comprised of the amino acid sequence defined in SEQ ID NOs: 1 or 2, or is a functional variant thereof, with a substitution at P57. In another embodiment, the above described mutant protein is comprised of the amino acid sequence defined in SEQ ID NOs: 4-8, or is a functional variant thereof, with a substitution at P57. The term "functional variant" as used in this context includes any similar sequence, which comprises one or more further variations in amino acid positions that have no influence on the mutant protein's affinity to immunoglobulins or its improved chemical stability in environments of increased pH-values.

In an advantageous embodiment, the present substitutions of P57 are selected from the group that consists of a bulky amino acid or amino acid giving "stiffness", e.g. Y, W, F, M, I, V, T; and wherein the parental molecule comprises the sequence defined by SEQ ID NO: 1-8, or any functional variance thereof. In other embodiments, P57 is substituted with an amino acids that is prone to formation of alpha helices, e.g. E, A, L, H, M, Q, K, and wherein the parental molecule comprises the sequence defined by SEQ ID NO: 1-8, or any functional variance thereof. More preferably, the substitution is P57I. As mentioned above, in order to achieve a mutant protein useful as a ligand with high binding capacity for a prolonged period of time in alkaline conditions, mutation of the asparagine residue in position 21 is avoided. In one embodiment, the asparagine residue in position 3 is not mutated.

In certain embodiments, the C-terminal most proline residue in at least one of the monomers in a multimeric ligand are substituted. In other embodiments, the C-terminal most proline residue in all the monomers in a multimeric ligand are substituted.

In one advantageous embodiment, an asparagine residue located between a leucine residue and a glutamine residue has also been mutated, for example to a threonine residue. Thus, in one embodiment, the asparagine residue in position 23 of the sequence defined in SEQ ID NO: 2 has been mutated, for example to a threonine residue. In a specific embodiment, the asparagine residue in position 43 of the sequence defined in SEQ ID NO: 2 has also been mutated, for example to a glutamic acid. In the embodiments where amino acid number 43 has been mutated, it appears to most advantageously be combined with at least one further mutation, such as N23T.

Thus, the invention encompasses the above-discussed monomeric mutant proteins. However, such protein monomers can be combined into multimeric ligands, such as dimers, trimers, tetramers, pentamers, hexamers etc. Accordingly, another aspect of the present invention is a multimer comprised of at least one of the mutated proteins according to the invention together with one or more further units, preferably also mutant proteins according to the invention. Thus, the present invention is e.g. a dimer comprised of two repetitive units, or a tetramer comprised of four repetitive units.

In certain embodiments, the multimeric ligands contain two or more, such as 2-4, copies of the same monomeric domain from domain E, D, A, B, C of protein A, or protein Z, or any functional variants.

In other embodiments, the multimeric ligands contain two or more, such as 2-4, different monomeric domains selected from domain E, D, A, B, C of protein A, or protein Z, or any functional variants.

In one embodiment, the multimer according to the invention comprises monomer units linked by a stretch of amino acids preferably ranging from 0 to 15 amino acids, such as 0-10 or 5-10 amino acids. The nature of such a link should preferably not destabilize the spatial conformation of the protein units. Furthermore, said link should preferably also be sufficiently stable in alkaline environments not to impair the properties of the mutated protein units.

In another embodiment, the present dimeric ligands comprise the sequence of SEQ ID NO: 3:

```
AlaGlnValAspAlaLysPheAspLysGluGlnGlnAsnAlaPheTyr
GluIleLeuHisLeuProAsnLeuThrGluGluGlnArgAsnAlaPhe
IleGlnSerLeuLysAspAspProSerGlnSerAlaAsnLeuLeuAla
GluAlaLysLysLeuAsnAspAlaGlnAlaIleLysValAspAlaLys
PheAspLysGluGlnGlnAsnAlaPheTyrGluIleLeuHisLeuPro
AsnLeuThrGluGluGlnArgAsnAlaPheIleGlnSerLeuLysAsp
AspProSerGlnSerAlaAsnLeuLeuAlaGluAlaLysLysLeuAsn
AspAlaGlnAlaIleLysCys
```

In a further embodiment, the dimeric ligands comprise the sequence of SEQ ID NO: 9:

```
AlaGlnValAspAsnLysPheAsnLysGluGlnGlnAsnAlaPheTyr
GluIleLeuHisLeuProAsnLeuThrGluGluGlnArgAsnGlyPhe
IleGlnSerLeuLysAspAspProSerValSerLysGluIleLeuAla
GluAlaLysLysLeuAsnAspAlaGlnAlaIleLysValAspAsnLys
PheAsnLysGluGlnGlnAsnAlaPheTyrGluIleLeuHisLeuPro
AsnLeuThrGluGluGlnArgAsnGlyPheIleGlnSerLeuLysAsp
AspProSerValSerLysGluIleLeuAlaGluAlaLysLysLeuAsn
AspAlaGlnAlaIleLysCys
```

In another embodiment, the tetrameric ligands comprise the sequence of SEQ ID NO: 10:

```
AlaGlnValAspAlaLysPheAspLysGluGlnGlnAsnAlaPheTyr
GluIleLeuHisLeuProAsnLeuThrGluGluGlnArgAsnAlaPhe
IleGlnSerLeuLysAspAspProSerGlnSerAlaAsnLeuLeuAla
GluAlaLysLysLeuAsnAspAlaGlnAlaIleLysValAspAlaLys
PheAspLysGluGlnGlnAsnAlaPheTyrGluIleLeuHisLeuPro
AsnLeuThrGluGluGlnArgAsnAlaPheIleGlnSerLeuLysAsp
AspProSerGlnSerAlaAsnLeuLeuAlaGluAlaLysLysLeuAsn
AspAlaGlnAlaIleLysValAspAlaLysPheAspLysGluGlnGln
AsnAlaPheTyrGluIleLeuHisLeuProAsnLeuThrGluGluGln
ArgAsnAlaPheIleGlnSerLeuLysAspAspProSerGlnSerAla
AsnLeuLeuAlaGluAlaLysLysLeuAsnAspAlaGlnAlaIleLys
ValAspAlaLysPheAspLysGluGlnGlnAsnAlaPheTyrGluIle
LeuHisLeuProAsnLeuThrGluGluGlnArgAsnAlaPheIleGln
SerLeuLysAspAspProSerGlnSerAlaAsnLeuLeuAlaGluAla
LysLysLeuAsnAspAlaGlnAlaIleLysCys
```

The current invention unexpectedly found that when comparing the capacity of the ligands, a substitution of the C-terminal proline (P57) in at least one of the monomeric domains of the ligand provides a higher capacity compared to non-substituted ligands.

One aspect of the invention relates to a ligand for separation of immunoglobulin containing proteins. The ligand comprises one or more domains of staphylococcal protein A (SpA) (E, D, A, C, C) or protein Z or a functional variant thereof, wherein the C-terminal most proline in at least one of the domains has been substituted with another amino acid. Such ligands provide for an increased immunoglobulin capacity when immobilised on solid support materials, compared to ligands which do not have this substitution. The ligand can be constructed according to any embodiment described above.

In one aspect, the invention relates to a matrix for affinity separation, which matrix comprises ligands that comprise immunoglobulin-binding protein coupled to a solid support. Preferably, the C-terminal most proline residue, in at least one of the monomeric domains of protein A (E, D, A, C, C) or protein Z, after the third alpha-helix, P57 residue has been substituted to another amino acid. Preferably, the ligands are multimeric, i.e., containing more than one monomeric domains selected from protein A (E, D, A, C, C) and protein Z. The present matrix, when compared to a matrix without the substitution, exhibits an increased binding capacity. The mutated protein ligand is preferably an Fc-fragment-binding protein, and can be used for selective binding of IgG, IgA and/or IgM, preferably IgG.

The matrix according to the invention can comprise the mutant protein as described above in any embodiment thereof as ligand. In the most preferred embodiment, the ligands present on the solid support comprise a substitution as described above.

The solid support of the matrix according to the invention can be of any suitable well-known kind. A conventional affinity separation matrix is often of organic nature and based on polymers that expose a hydrophilic surface to the aqueous media used, i.e. expose hydroxy (—OH), carboxy (—COOH), carboxamido (—CONH$_2$, possibly in N-substituted forms), amino (—NH$_2$, possibly in substituted form), oligo- or polyethylenoxy groups on their external and, if present, also on internal surfaces. In one embodiment, the polymers may, for instance, be based on polysaccharides, such as dextran, starch, cellulose, pullulan, agar, agarose etc, which advantageously have been cross-linked, for instance with bisepoxides, epihalohydrins, 1,2,3-trihalo substituted lower hydrocarbons or according to the methods described in U.S. Pat. No. 6,602,990, to provide a suitable porosity and rigidity. In the most preferred embodiment, the solid support is porous agar or agarose beads. The supports used in the present invention can easily be prepared according to standard methods, such as inverse suspension gelation (S Hjertén: Biochim Biophys Acta 79(2), 393-398 (1964). Alternatively, the base matrices are commercially available products, such as Sepharose™ FF or Sepharose HP (GE Healthcare). In an embodiment, which is especially advantageous for large-scale separations, the support has been adapted to increase its rigidity, and hence renders the matrix more suitable for high flow rates.

Alternatively, the solid support is based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare) is used.

In another alternative, the solid support according to the invention comprises a support of inorganic nature, e.g. silica, zirconium oxide etc.

In yet another embodiment, the solid support is in another form such as a surface, a chip, capillaries, or a filter.

As regards the shape of the matrix according to the invention, in one embodiment the matrix is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batch-wise mode will be used.

The ligand may be attached to the support via conventional coupling techniques utilising, e.g. amino and/or carboxy groups present in the ligand. Bisepoxides, epichlorohydrin, CNBr, N-hydroxysuccinimide (NHS) etc are well-known coupling reagents. Between the support and the ligand, a molecule known as a spacer can be introduced, which will improve the availability of the ligand and facilitate the chemical coupling of the ligand to the support. Alternatively, the ligand may be attached to the support by non-covalent bonding, such as physical adsorption or biospecific adsorption. The ligand content of the matrix may be 5-15 mg/ml matrix and can advantageously be 5-10 mg/ml.

In an advantageous embodiment, the present ligand has been coupled to the support by thioether bonds. Methods for performing such coupling are well-known in this field and easily performed by the skilled person in this field using standard techniques and equipment. In an advantageous embodiment, the ligand is firstly provided with a terminal cysteine residue for subsequent use in the coupling. The skilled person in this field also easily performs appropriate steps of purification.

In certain embodiments of the invention, the conditions for the adsorption step may be any conventionally used, appropriately adapted depending on the properties of the target antibody such as the pI thereof. The optional wash step can be performed using a buffer commonly used such as a PBS buffer.

The elution may be performed by using any commonly used buffer.

The present method is useful to capture target antibodies, such as a first step in a purification protocol of antibodies which are e.g. for therapeutic or diagnostic use. In one embodiment, at least 75% of the antibodies are recovered. In an advantageous embodiment, at least 80%, such as at least 90%, and preferably at least 95% of the antibodies are recovered using an eluent having a suitable pH for the particular ligand system. The present method may be followed by one or more additional steps, such as other chromatography steps. Thus, in a specific embodiment, more than about 98% of the antibodies are recovered.

As discussed earlier, for either SpA (domain E, D, A, B, C) or protein Z ligand, when at least one asparagine residue is mutated to an amino acid other than glutamine or aspartic acid, affinity media including these mutant ligands can better withstand cleaning procedures using alkaline agents (US 2005/0143566). The increased stability means that the mutated protein's initial affinity for immunoglobulin is essentially retained for a prolonged period of time. Thus its binding capacity will decrease more slowly than that of the parental molecule in an alkaline environment. The environment can be defined as alkaline, meaning of an increased pH-value, for example above about 10, such as up to about 13 or 14, i.e. from 10-13 or 10-14, in general denoted alkaline conditions. Alternatively, the conditions can be defined by the concentration of NaOH, which can be up to about 1.0 M, such as 0.7 M or specifically about 0.5 M, accordingly within a range of 0.7-1.0 M.

Thus, the affinity to immunoglobulin i.e. the binding properties of the present ligand, in the presence of the asparagine mutation as discussed, and hence the capacity of the matrix, is not essentially changed in time by treatment with an alkaline agent. Conventionally, for a cleaning in place treatment of an affinity separation matrix, the alkaline agent used is NaOH and the concentration thereof is up to 0.75 M, such as 0.5 M. Thus, its binding capacity will decrease to less than about 70%, preferably less than about 50% and more preferably less than about 30%, such as about 28%, after treatment with 0.5 M NaOH for 7.5 h.

In a further aspect, the present invention relates to a method of isolating an immunoglobulin, such as IgG, IgA and/or IgM, wherein a ligand or a matrix according to the invention is used. Thus, the invention encompasses a process of chromatography, wherein at least one target compound is separated from a liquid by adsorption to a ligand or matrix described above. The desired product can be the separated compound or the liquid. Thus, this aspect of the invention relates to affinity chromatography, which is a widely used and well-known separation technique. In brief, in a first step, a solution comprising the target compounds, preferably antibodies as mentioned above, is passed over a separation matrix under conditions allowing adsorption of the target compound to ligands present on said matrix. Such conditions are controlled e.g. by pH and/or salt concentration i.e. ionic strength in the solution. Care should be taken not to exceed the capacity of the matrix, i.e. the flow should be sufficiently slow to allow a satisfactory adsorption. In this step, other components of the solution will pass through in principle unimpeded. Optionally, the matrix is then washed, e.g. with an aqueous solution, in order to remove retained and/or loosely bound substances. The present matrix is most advantageously used with an intermediate washing step utilizing additives such as solvents, salts or detergents or mixture there of. In a next step, a second solution denoted an eluent is passed over the matrix under conditions that provide desorption i.e. release of the target compound. Such conditions are commonly provided by a change of the pH, the salt concentration i.e. ionic strength, hydrophobicity etc. Various elution schemes are known, such as gradient elution and step-wise elution. Elution can also be provided by a second solution comprising a competitive substance, which will replace the desired antibody on the matrix. For a general review of the principles of affinity chromatography, see e.g. Wilchek, M., and Chaiken, I. 2000. An overview of affinity chromatography. *Methods Mol. Biol.* 147: 1-6.

EXAMPLES

Below, the present invention will be described by way of examples, which are provided for illustrative purposes only and accordingly are not to be construed as limiting the scope of the present invention as defined by the appended claims.

All references given below and elsewhere in this application are hereby included herein by reference.

Example 1

Prototypes

Mutant Z(P57I)2: ligand dimers containing two copies of protein Z, each containing the P57I substitution (Z(P57I)2) (SEQ ID No. 3), with ligand density of 5.8 mg/ml.

Mutant Z(P57I)4: ligand tetramers containing four copies of protein Z, each containing the P57I substitution (Z(P57I)4) (SEQ ID No. 10), with ligand density of 9.7 mg/ml.

Mutant C(P57I)2: ligand dimers containing two copies of the Protein A C domain, each containing the P57I substitution (C(P57I)2) (SEQ ID No. 9), with ligand density of 7.2 mg/ml.

Regular Z2: ligand dimers containing two copies of protein Z (Z2 reg) (SEQ ID No. 3 but without the P57I substitutions), with ligand density of 6.1 mg/ml.

2 ml of each resin was packed in Tricorn 5 100 columns
Protein
    Gammanorm 165 mg/ml (Octapharma), diluted to 1 mg/ml in Equilibration buffer.
Equilibration Buffer
    APB Phosphate buffer 20 mM+0.15M NaCl, pH 7,4 (Elsichrom AB)
Adsorption Buffer
    APB Phosphate buffer 20 mM+0.15M NaCl, pH 7.4 (Elsichrom AB).
Elution Buffer
    APB Citrate buffer 0.1M, pH 3 (Elsichrom AB).
CIP
    0.1M NaOH.
Experimental Details and Results:
Mutagenesis of Protein Site-directed mutagenesis was performed by PCR using an oligonucleotide coding for the pro-line replacement. As template a plasmid containing a single domain of either Z or C was used. The PCR fragments were ligated into an *E. coli* expression vector (pGO). DNA sequencing was used to verify the correct sequence of inserted fragments.

To form multimers of Z(P57I) and C(P57I) an Acc I site located in the starting codons (GTA GAC) of the C or Z domain was used, corresponding to amino acids VD. pGO Z(P57I)1 and pGO C(P57I)1 were digested with Acc I and CIP treated. Acc I sticky-ends primers were designed, specific for each variant, and two overlapping PCR products were generated from each template. The PCR products were purified and the concentration was estimated by comparing the PCR products on a 2% agarose gel. Equal amounts of the pair wise PCR products were hybridized (90° C.->25° C. in 45 min) in ligation buffer. The resulting product consists approximately to ¼ of fragments likely to be ligated into an Acc I site (correct PCR fragments and/or the digested vector). After ligation and transformation colonies were PCR screened to identify constructs containing Z(P57I)2, Z(P57I)4, C(P57I)2 and C(P57I)4. Positive clones were verified by DNA sequencing.

Construct Expression and Purification

The constructs were expressed in the bacterial periplasm by fermentation of *E. coli* K12 in standard media. After fermentation the cells were heat-treated to release the periplasm content into the media. The constructs released into the medium were recovered by microfiltration with a membrane having a 0.2 μm pore size.

Each construct, now in the permeate from the filtration step, was purified by affinity. The permeate was loaded onto a chromatography medium containing immobilized IgG. The loaded product was washed with phosphate buffered saline and eluted by lowering the pH.

The elution pool was adjusted to a neutral pH and reduced by addition of dithio threitol. The sample was then loaded onto an anion exchanger. After a wash step the construct was eluted in a NaCl gradient to separate it from any contaminants. The elution pool was concentrated by ultra-filtration to 40-50 mg/ml.

The purified ligands were analyzed with LC-MS to determine the purity and to ascertain that the molecular weight corresponded to the expected (based on the amino acid sequence).

Activation

The base matrix used was rigid crosslinked agarose beads of 85 microns average diameter, prepared according to the methods of U.S. Pat. No. 6,602,990 and with a pore size corresponding to an inverse gel filtration chromatography Kav value of 0.70 for dextran of Mw 110 kDa, according to the methods described in Gel Filtration Principles and Methods, Pharmacia LKB Biotechnology 1991, pp 6-13.

25 mL (g) of drained base matrix, 10.0 mL distilled water and 2.02 g NaOH (s) was mixed in a 100 mL flask with mechanical stirring for 10 min at 25° C. 4.0 mL of epichlorohydrin was added and the reaction progressed for 2 hours. The activated gel was washed with 10 gel sediment volumes (GV) of water.

Coupling

To 20 mL of ligand solution (50 mg/mL) in a 50 ml Falcon tube, 169 mg NaHCO$_3$, 21 mg Na$_2$CO$_3$, 175 mg NaCl and 7 mg EDTA, was added. The Falcon tube was placed on a roller table for 5-10 min, and then 77 mg of DTE was added. Reduction proceeded for >45 min The ligand solution was then desalted on a PD10 column packed with Sephadex G-25. The ligand content in the desalted solution was determined by measuring the 276 nm UV absorption.

The activated gel was washed with 3-5 GV {0.1 M phosphate/1 mM EDTA pH 8.6} and the ligand was then coupled according to the method described in U.S. Pat. No. 6,399,750. All buffers used in the experiments had been degassed by nitrogen gas for at least 5-10 min.

After immobilisation the gels were washed 3×GV with distilled water. The gels+1 GV {0.1 M phosphate/1 mM EDTA/10% thioglycerol pH 8.6} was mixed and the tubes were left in a shaking table at room temperature over night. The gels were then washed alternately with 3×GV {0.1 M TRIS/0.15 M NaCl pH 8.6} and 0.5 M HAc and then 8-10× GV with distilled water. Gel samples were sent to an external laboratory for amino acid analysis and the ligand content (mg/ml gel) was calculated from the total amino acid content.

Capacity Determination

The breakthrough capacity was determined with an ÄKTAExplorer 10 system at a residence time of 2.4 and 6 min as standard. Adsorption buffer was run through the bypass column until a stable baseline was obtained. This was done prior to auto zeroing. Sample was applied to the column until a 100% UV signal was obtained. Then, adsorption buffer was applied again until a stable baseline.

The column was equilibrated with adsorption buffer prior to loading with sample until a UV signal of 85% of maximum absorbance was reached. The column was then washed with adsorption buffer until a UV signal of 20% of maximum absorbance at flow rate 0.5 ml/min. The protein was eluted with 10 CV elution buffer at flow rate 0.5 ml/min. Then the column was cleaned with 0.1M NaOH at flow rate 0.5 ml/min and re-equilibrated with adsorption buffer prior to cleaning with 20% ethanol. The last step was to check the sample concentration by loading sample through the bypass column until a 100% UV signal was obtained.

For calculation of breakthrough capacity at 10%, the equation below was used. That is the amount of IgG that is loaded onto the column until the concentration of IgG in the column effluent is 10% of the IgG concentration in the feed.

$$q_{10\%} = \frac{C_0}{V_c}\left[V_{app} - V_{sys} - \int_{V_{sys}}^{V_{app}} \frac{A(V) - A_{sub}}{A_{100\%} - A_{sub}} * dv\right]$$

$A_{100\%}$=100% UV signal;
$A_{sub}$=absorbance contribution from non-binding IgG subclass;
$A(V)$=absorbance at a given applied volume;
$V_c$=column volume;
$V_{app}$=volume applied until 10% breakthrough;
$V_{sys}$=system dead volume;
$C_0$=feed concentration.

Figure 3:
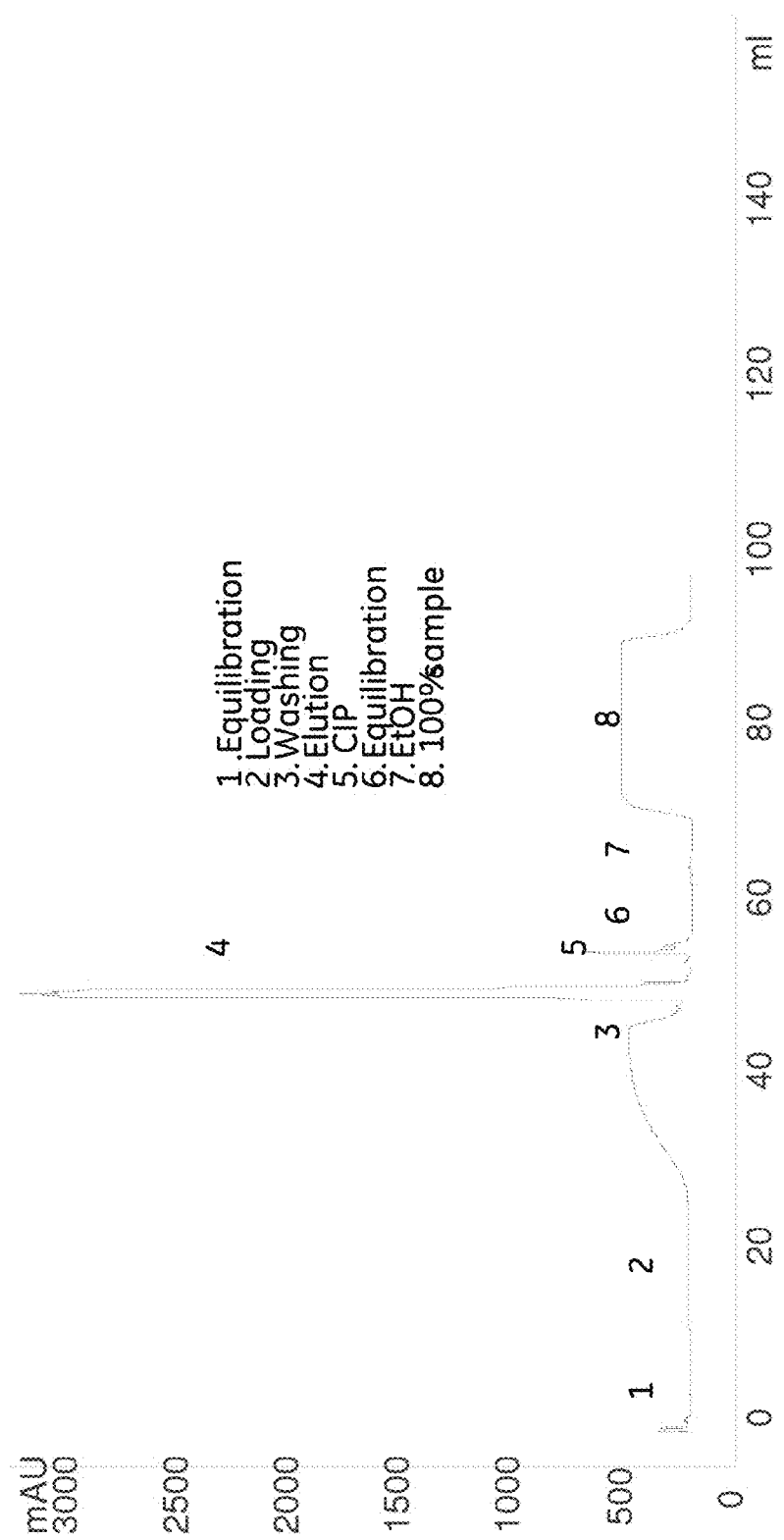
FIG. 3 shows a representative chromatogram result for dynamic binding capacity assay.

A typical run for dynamic binding capacity is shown in FIG. 3. The dynamic binding capacity (DBC) at 10% breakthrough was calculated and the appearance of the curve was studied. The curve was also studied regarding binding, elution and CIP peak.

The dynamic binding capacity (DBC) was calculated for 5, 10 and 80% breakthrough. Results are shown in Table 1. Higher capacity was observed for ligands with P57I substitution as compared to the parental P57 ligand.

TABLE 1

Summary of results.

| Prototype (two columns were packed and tested) | Ligand density (mg/ml resin) | Qb5 (mg/ml resin) | Qb10 (mg/ml resin) | Qb80 (mg/ml resin) | Res time (min) |
|---|---|---|---|---|---|
| Z(P57I)2#1 | 5.8 | 31.5 | 34.3 | 51 | 2.4 |
| Z(P57I)2#2 | 5.8 | 33.5 | 35.7 | 51.8 | 2.4 |
| Z(P57I)2#2 | 5.8 | 32.4 | 34.6 | 50.3 | 2.4 |
| Z(P57I)2#2 | 5.8 | 34.0 | 36.2 | 53.4 | 2.4 |
| Z(P57I)2#1 | 5.8 | 44.1 | 45.6 | 53.5 | 6.0 |
| Z(P57I)2#2 | 5.8 | 43.9 | 45.6 | 53.6 | 6.0 |
| Z(P57I)2#2 | 5.8 | 42.6 | 44.6 | na | 6.0 |
| Z(P57I)2#2 | 5.8 | 45.4 | 46.6 | 54.5 | 6.0 |
| Z2reg#1 | 6.1 | 28.5 | 31.4 | 43.8 | 2.4 |
| Z2reg#2 | 6.1 | 29.9 | 32.2 | 46.1 | 2.4 |
| Z2reg#1 | 6.1 | 38.1 | 40.6 | 46.7 | 6.0 |
| Z2reg#2 | 6.1 | 38.5 | 40.4 | 47.1 | 6.0 |
| C(P57I)2 | 7.2 | 36.9 | 40.2 | 63.7 | 2.4 |
| C(P57I)2 | 7.2 | 52.6 | 55.2 | 66.9 | 6.0 |
| Z(P57I)4 | 9.7 | 35.2 | 39.0 | 68.0 | 2.4 |
| Z(P57I)4 | 9.7 | 54.7 | 57.1 | 72.4 | 6.0 |

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims. It is further understood that features of different embodiments can be combined.

What is claimed is:

1. A ligand for separation of immunoglobulin containing proteins, which ligand comprises one or more monomeric domains of staphylococcal protein A (SpA) (E, D, A, B, C) or protein Z, wherein the proline nearest the C terminus in at least one of the domains has been substituted with any other amino acid.

2. The ligand of claim 1, wherein said one or more domains of protein A or protein Z are two or more copies from the same domain of SpA (E, D, A, B, C) or protein Z respectively.

3. The ligand of claim 1, wherein the proline nearest the C terminus in at least one of the monomers in a multimeric ligand has been substituted with another amino acid.

4. The ligand of claim 1, wherein the proline nearest the C terminus in all the monomers in a multimeric ligand have been substituted with another amino acid.

5. The ligand of claim 1, wherein the proline nearest the C terminus in at least one monomer is substituted with an amino acid selected from Y, W, F, M, I, V, T.

6. The ligand of claim 1, wherein the proline nearest the C terminus in at least one monomer is substituted with isoleucine.

7. The ligand of claim 1, wherein the proline nearest the C terminus in at least one monomer is substituted with an amino acid selected from E, A, L, H, M, Q, K.

8. The ligand of claim 1, wherein the ligand achieves alkali stability by mutating at least one asparagine residue to an amino acid other than glutamine.

9. The ligand of claim 1, wherein the ligand has affinity for the Fc part of an immunoglobulin but lacks affinity for the Fab part of an immunoglobulin.

10. The ligand of claim 1, wherein at least one glycine of said ligands has been replaced by an alanine.

11. The ligand of claim 1, wherein the ligand is protein Z in which the alkali-stability has been achieved by mutating at least one asparagine residue to an amino acid other than glutamine.

12. The ligand of claim 11, wherein the alkali-stability of protein Z has been achieved by mutating at least the asparagine residue at position 23 to an amino acid other than glutamine.

13. The ligand of claim 1, wherein said multimer is a dimer or a tetramer.

* * * * *

SEQUENCE LISTING

<160> NUMBER OF SEQ ID NOS: 10

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 2
<211> LENGTH: 58
<212> TYPE: PRT
<213> ORGANISM: Escherichia coli

<400> SEQUENCE: 2

Val Asp Ala Lys Phe Asp Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 3
<211> LENGTH: 119
<212> TYPE: PRT
<213> ORGANISM: Escherichia coli

<400> SEQUENCE: 3

Ala Gln Val Asp Ala Lys Phe Asp Lys Glu Gln Gln Asn Ala Phe Tyr
1               5                   10                  15

Glu Ile Leu His Leu Pro Asn Leu Thr Glu Glu Gln Arg Asn Ala Phe
            20                  25                  30

Ile Gln Ser Leu Lys Asp Asp Pro Ser Gln Ser Ala Asn Leu Leu Ala
        35                  40                  45

Glu Ala Lys Lys Leu Asn Asp Ala Gln Ala Ile Lys Val Asp Ala Lys
    50                  55                  60

Phe Asp Lys Glu Gln Gln Asn Ala Phe Tyr Glu Ile Leu His Leu Pro
65                  70                  75                  80

Asn Leu Thr Glu Glu Gln Arg Asn Ala Phe Ile Gln Ser Leu Lys Asp
                85                  90                  95

Asp Pro Ser Gln Ser Ala Asn Leu Leu Ala Glu Ala Lys Lys Leu Asn
            100                 105                 110

Asp Ala Gln Ala Ile Lys Cys
        115

<210> SEQ ID NO 4
<211> LENGTH: 50
<212> TYPE: PRT
<213> ORGANISM: Staphylococcus aureus

```
<400> SEQUENCE: 4

Gln Gln Asn Ala Phe Tyr Gln Val Leu Asn Met Pro Asn Leu Asn Ala
1               5                   10                  15

Asp Gln Arg Asn Gly Phe Ile Gln Ser Leu Lys Asp Asp Pro Ser Gln
            20                  25                  30

Ser Ala Asn Val Leu Gly Glu Ala Gln Lys Leu Asn Asp Ser Gln Ala
        35                  40                  45

Pro Lys
    50

<210> SEQ ID NO 5
<211> LENGTH: 61
<212> TYPE: PRT
<213> ORGANISM: Staphylococcus aureus

<400> SEQUENCE: 5

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60

<210> SEQ ID NO 6
<211> LENGTH: 58
<212> TYPE: PRT
<213> ORGANISM: Staphylococcus aureus

<400> SEQUENCE: 6

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55

<210> SEQ ID NO 7
<211> LENGTH: 58
<212> TYPE: PRT
<213> ORGANISM: Staphylococcus aureus

<400> SEQUENCE: 7

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT
```

<213> ORGANISM: Staphylococcus aureus

<400> SEQUENCE: 8

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 9
<211> LENGTH: 119
<212> TYPE: PRT
<213> ORGANISM: Escherichia coli

<400> SEQUENCE: 9

Ala Gln Val Asp Asn Lys Phe Asn Lys Glu Gln Gln Asn Ala Phe Tyr
1               5                   10                  15

Glu Ile Leu His Leu Pro Asn Leu Thr Glu Glu Gln Arg Asn Gly Phe
            20                  25                  30

Ile Gln Ser Leu Lys Asp Asp Pro Ser Val Ser Lys Glu Ile Leu Ala
        35                  40                  45

Glu Ala Lys Lys Leu Asn Asp Ala Gln Ala Ile Lys Val Asp Asn Lys
    50                  55                  60

Phe Asn Lys Glu Gln Gln Asn Ala Phe Tyr Glu Ile Leu His Leu Pro
65                  70                  75                  80

Asn Leu Thr Glu Glu Gln Arg Asn Gly Phe Ile Gln Ser Leu Lys Asp
                85                  90                  95

Asp Pro Ser Val Ser Lys Glu Ile Leu Ala Glu Ala Lys Lys Leu Asn
            100                 105                 110

Asp Ala Gln Ala Ile Lys Cys
        115

<210> SEQ ID NO 10
<211> LENGTH: 235
<212> TYPE: PRT
<213> ORGANISM: Escherichia coli

<400> SEQUENCE: 10

Ala Gln Val Asp Ala Lys Phe Asp Lys Glu Gln Gln Asn Ala Phe Tyr
1               5                   10                  15

Glu Ile Leu His Leu Pro Asn Leu Thr Glu Glu Gln Arg Asn Ala Phe
            20                  25                  30

Ile Gln Ser Leu Lys Asp Asp Pro Ser Gln Ser Ala Asn Leu Leu Ala
        35                  40                  45

Glu Ala Lys Lys Leu Asn Asp Ala Gln Ala Ile Lys Val Asp Ala Lys
    50                  55                  60

Phe Asp Lys Glu Gln Gln Asn Ala Phe Tyr Glu Ile Leu His Leu Pro
65                  70                  75                  80

Asn Leu Thr Glu Glu Gln Arg Asn Ala Phe Ile Gln Ser Leu Lys Asp
                85                  90                  95

Asp Pro Ser Gln Ser Ala Asn Leu Leu Ala Glu Ala Lys Lys Leu Asn
            100                 105                 110

Asp Ala Gln Ala Ile Lys Val Asp Ala Lys Phe Asp Lys Glu Gln Gln
        115                 120                 125

```
Asn Ala Phe Tyr Glu Ile Leu His Leu Pro Asn Leu Thr Glu Glu Gln
    130                 135             140

Arg Asn Ala Phe Ile Gln Ser Leu Lys Asp Asp Pro Ser Gln Ser Ala
145                 150             155                 160

Asn Leu Leu Ala Glu Ala Lys Lys Leu Asn Asp Ala Gln Ala Ile Lys
                165             170             175

Val Asp Ala Lys Phe Asp Lys Glu Gln Gln Asn Ala Phe Tyr Glu Ile
            180             185             190

Leu His Leu Pro Asn Leu Thr Glu Glu Gln Arg Asn Ala Phe Ile Gln
        195             200             205

Ser Leu Lys Asp Asp Pro Ser Gln Ser Ala Asn Leu Leu Ala Glu Ala
    210             215             220

Lys Lys Leu Asn Asp Ala Gln Ala Ile Lys Cys
225             230             235
```